(12) United States Patent
Yoo et al.

(10) Patent No.: US 9,299,174 B2
(45) Date of Patent: Mar. 29, 2016

(54) SYNTHETIC APERTURE BEAM FORMING METHOD AND APPARATUS OF DETERMINING NUMBER OF SYNTHETIC BEAMS ACCORDING TO DEGREE OF MOTION

(75) Inventors: Yang Mo Yoo, Goyang-si (KR); Tai-Kyong Song, Seoul (KR); Jin Ho Chang, Seoul (KR); Jeong Cho, Seoul (KR); Jong Ho Park, Incheon (KR)

(73) Assignee: INDUSTRY-UNIVERSITY COOPERATION FOUNDATION SOGANG UNIVERSITY (KR)

( * ) Notice: Subject to any disclaimer, the term of this patent is extended or adjusted under 35 U.S.C. 154(b) by 430 days.

(21) Appl. No.: 13/981,690

(22) PCT Filed: Jan. 13, 2012

(86) PCT No.: PCT/KR2012/000340
§ 371 (c)(1),
(2), (4) Date: Sep. 4, 2013

(87) PCT Pub. No.: WO2012/102503
PCT Pub. Date: Aug. 2, 2012

(65) Prior Publication Data
US 2013/0335423 A1    Dec. 19, 2013

(30) Foreign Application Priority Data
Jan. 27, 2011 (KR) .......................... 10-2011-0008399

(51) Int. Cl.
*G06T 11/20* (2006.01)
*G01S 15/89* (2006.01)
*A61B 8/00* (2006.01)
*G01S 7/52* (2006.01)

(52) U.S. Cl.
CPC .............. *G06T 11/206* (2013.01); *A61B 8/585* (2013.01); *G01S 15/8997* (2013.01); *A61B 8/463* (2013.01); *G01S 7/5205* (2013.01); *G01S 7/52073* (2013.01)

(58) Field of Classification Search
None
See application file for complete search history.

(56) References Cited

U.S. PATENT DOCUMENTS

| | | | |
|---|---|---|---|
| 6,736,780 B2 | 5/2004 | Song et al. | |
| 7,645,236 B2 | 1/2010 | Simopoulos et al. | |
| 2009/0112092 A1 | 4/2009 | Bae et al. | |
| 2010/0260398 A1* | 10/2010 | Ma | A61B 6/469 382/131 |
| 2013/0261463 A1* | 10/2013 | Chiang | A61B 8/14 600/447 |
| 2014/0071792 A1* | 3/2014 | Yoo | G01S 7/52047 367/103 |

FOREIGN PATENT DOCUMENTS

KR    1020090057837    6/2009

OTHER PUBLICATIONS

International Search Report—PCT/KR2012/000340 dated Sep. 24, 2012.

* cited by examiner

*Primary Examiner* — Peter Hoang
(74) *Attorney, Agent, or Firm* — Cantor Colburn LLP

(57) ABSTRACT

Provided is an apparatus of determining the number of synthetic beams, comprising: a motion measurement unit which measures the degree of motion in an output beam-forming image; a synthetic beam number determination unit which determines the optimum number of synthetic beams based on the measured degree of motion in case of applying the synthetic aperture beam forming; and a display unit which displays the number of synthetic beams determined by the synthetic beam number determination unit. A system using synthetic aperture beam forming detects motion in an image and displays a degree of the motion in various manners, and thus, a user is allowed to actively cope with the motion by adjusting the number of synthetic beams, or the system is allowed to immediately change the number of synthetic beams with reference to data stored in advance.

17 Claims, 5 Drawing Sheets

(a)

(b)

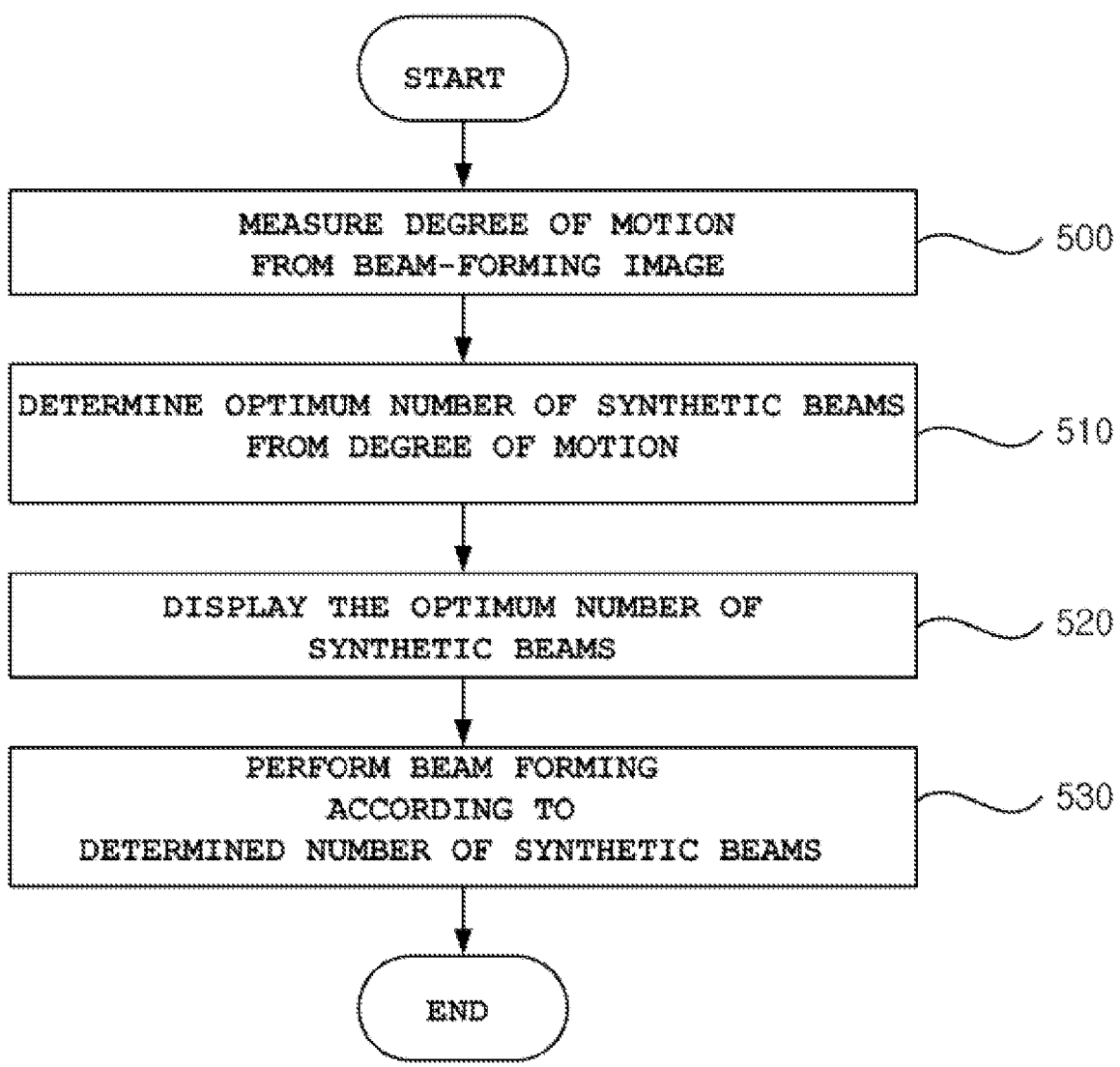

SYNTHETIC APERTURE BEAM FORMING METHOD AND APPARATUS OF DETERMINING NUMBER OF SYNTHETIC BEAMS ACCORDING TO DEGREE OF MOTION

TECHNICAL FIELD

The present invention relates to a synthetic aperture beam forming apparatus, and more particularly, and a synthetic aperture beam forming apparatus of detecting motion in an image, displaying a degree of the motion on a screen in various manners, and allowing a system to automatically determine the number of synthetic beams with reference to values of parameters stored in advance so as to actively cope with the motion or allowing a user to manually determine the number of synthetic beams with reference to a degree of motion displayed on the screen.

BACKGROUND ART

In a conventional dynamic focusing (CDF) where one scan line is configured by using single transmission/reception process, focused signals can be obtained in all regions on the scan line of a received beam. However, in the CDF, since single focusing point is fixed in the reception process, resolution is low in regions other than the focusing point.

On the other hand, in synthetic aperture (SA) beam forming, since the focused signal can be obtained in all the transmission and reception regions, high-resolution image can be obtained in comparison to the CDF.

In the synthetic aperture beam forming, transmission and reception processes are sequentially performed by using subapertures constructed with a certain number of conversion elements, and acquired reception signals are combined to each other with an optimum delay time being applied, so that each scan line is configured. Since an effect of focusing ultrasonic waves can be obtained by using a synthetic aperture corresponding to a total size of the subapertures used for configuring each scan line, resolution can be effectively improved. However, in the synthetic aperture beam forming, since signals transmitted and received by using several adjacent subapertures are used for configuring one scan line. Therefore, unlike the CDF, the synthetic aperture beam forming is very sensitive to shaking of ultrasonic wave converters, motion of an object, or motion of an organ in a human body, and the like. The above-mentioned motions lead to non-uniformity of acoustic characteristics in a humane organ and phase distortion of received echo signals, so that the performance of ultrasonic wave focusing is deteriorated. Therefore, in order to observe an image of a fast-moving object by using the synthetic aperture beam forming, the defects regarding to the motion need to be overcome.

DISCLOSURE

Technical Problem

The present invention is to provide an apparatus of determining the optimum number of synthetic beams, which detects motion in an image and displays the motion on a screen in various manners to allow a user to be informed that error in focusing according to the motion of an object in case of using synthetic aperture beam forming and to actively cope with the motion by increasing or decreasing the number of synthetic beams, limiting patient's motion or the like.

The present invention is also to provide a synthetic aperture beam forming apparatus which detects motion in an image, displays the motion on a screen in various manners, determines automatically the optimum number of synthetic beams according to user's selection and generates synthetic beams according to the number of synthetic beams.

The present invention is also to provide a method of determining the optimum number of synthetic beams, which detects degree of motion in an image and displays the degree of the motion on a screen in various manners to allow a user to actively cope with the degree of the motion by adjusting the number of synthetic beams.

The present invention is also to provide a synthetic aperture beam forming method, which detects motion in an image and displays a degree of the motion on a screen in various manners to allow a user to actively cope with the degree of the motion by adjusting the number of synthetic beams.

The present invention is also to provide a computer-readable recording medium with a program recorded thereon for allowing a computer to execute the above-mentioned method.

Technical Solution

According to an aspect of the present invention, there is provided an apparatus of determining the number of synthetic beams according to a degree of motion by using synthetic aperture beam forming, comprising: a motion measurement unit which measures the degree of motion in an output beam-forming image; a synthetic beam number determination unit which determines the number of synthetic beams based on the measured degree of motion in case of applying the synthetic aperture beam forming; and a display unit which displays the number of synthetic beams determined by the synthetic beam number determination unit.

According to the above aspect, the synthetic beam number determination unit may automatically determine the number of synthetic beams based on the measured degree of motion.

In addition, the display unit may display stability of a beam-forming image corresponding to the number of synthetic beams, and the number of synthetic beams selected by a user with reference to the stability corresponding to the number of synthetic beams may be input to the synthetic beam number determination unit.

In addition, the display unit may display the degree of motion by representing the number of arrows according to the degree of motion in the beam-forming image, and the number of synthetic beams selected by a user with reference to the number of arrows may be input to the synthetic beam number determination unit.

In addition, the display unit may display the degree of motion by using a parameter bar, and the number of synthetic beams selected by a user with reference to the parameter bar may be input to the synthetic beam number determination unit.

In addition, the motion measurement unit may compare an image of a previous frame to an image of a current frame in the beam-forming image by using a block matching algorithm, and after that, measure the degree of motion by using a result of the comparison.

In addition, the motion measurement unit may measure the degree of motion by using correlation between focused beams by using a plurality of subapertures in scan lines or image points in the beam-forming image.

In addition, the motion measurement unit may measure representative motion in a region of interest, and the representative motion may be motion at a point where energy of a focused signal has the maximum value in the region of interest.

In addition, the motion measurement unit may measure representative motion or an average motion speed in a region of interest by using an autocorrelation based Doppler average frequency estimation method.

In addition, the motion measurement unit may compare an image of a previous frame to an image of a current frame in the beam-forming image by using a block matching algorithm, and after that, estimate motion in units of pixels. In addition, the motion measurement unit may convert the motion in units of pixels into a speed with reference to system parameters, so that the speed in the calculated block can be estimated.

In addition, a relationship between the measured degree of motion and the optimum number of synthetic beams for generating a stabilized beam-forming image may be determined in advance to be stored in a table.

According to another aspect of the present invention, there is provided a synthetic aperture beam forming apparatus of determining the number of synthetic beams according to a degree of motion, comprising: a motion measurement unit which measures the degree of motion in an output beam-forming image; a synthetic beam number determination unit which determines the optimum number of synthetic beams based on the measured degree of motion in case of applying the synthetic aperture beam forming; a display unit which displays the number of synthetic beams determined by the synthetic beam number determination unit; and a synthetic aperture beam forming unit which performs beam forming according to the number of synthetic beams determined by the synthetic beam number determination unit.

In the above aspect, a relationship between the measured degree of motion and the optimum number of synthetic beams, which can be obtained a stabilized beam-forming image, may be determined in advance to be stored in a table.

In addition, the determined number of synthetic beams is immediately applied as a parameter to the synthetic aperture beam forming unit, so that the synthetic aperture beam forming unit can be performed.

In addition, the determined synthetic beams is automatically applied to the synthetic aperture beam forming unit or is displayed through the display unit to the user according to the user's selection, so that the user can select the number of synthetic beams.

According to still another aspect of the present invention, there is provided a method of determining the number of synthetic beams, comprising steps of: measuring the degree of motion of an output beam-forming image; determining the number of synthetic beams based on the measured degree of motion in case of applying the synthetic aperture beam forming; and displaying the determined number of synthetic beams.

According to further still another aspect of the present invention, there is provided a synthetic aperture beam forming of determining the number of synthetic beams according to a degree of motion, comprising steps of: measuring the degree of motion of an output beam-forming image; determining the number of synthetic beams based on the measured degree of motion in case of applying the synthetic aperture beam forming; displaying the determined number of synthetic beams; and performing beam forming by generating the synthetic beams according to the determined number of synthetic beams.

According to yet further still another aspect of the present invention, there is provided a computer-readable recording medium with a program recorded thereon for allowing a computer to execute the method of determining the number of synthetic beams according to a degree of motion by using synthetic aperture beam forming the synthetic aperture beam forming method.

Advantageous Effects

According to the present invention, a system using synthetic aperture beam forming detects motion in an image and displays the motion in various manners, and a user is allowed to actively cope with the motion by adjusting the number of synthetic beams, or the system is allowed to select the optimum number of synthetic beams with reference to information recorded in advance and to perform a process by using the number of synthetic beams, so that it is possible to reduce error according to the motion.

BRIEF DESCRIPTION OF DRAWINGS

FIG. 5 is a flowchart illustrating a synthetic aperture beam forming method of determining the number of synthetic beams according to a degree of motion according to another embodiment of the present invention.

BEST MODE

First, for the better understanding of the present invention, a review of solutions to the problems and a gist of technical matter will be disclosed before detailed description of the present invention.

According to an embodiment of the present invention, an apparatus of determining the number of synthetic beams includes a motion measurement unit which measures a degree of motion in an output beam-forming image; a synthetic beam number determination unit which determines the number of synthetic beams based on the measured degree of motion in the case of applying the synthetic aperture beam forming; and a display unit which displays the number of synthetic beams determined by the synthetic beam number determination unit.

Mode for Invention

Hereinafter, exemplary embodiments of the present invention will be described more in detail. It will be understood by the ordinarily skilled in the related art that the embodiments are provided for detailed description of the invention but the present invention is not limited thereto. The configuration of the present invention for clarifying the solutions to the problems will be described in detail based on the embodiments with reference to attached drawings. In addition, detailed description of well-known functions or configurations regarding to the present invention may be omitted in the case where the present invention is determined to unnecessarily become unclear due to the detailed description.

In the case where synthetic aperture (SA) beam forming is applied to an ultrasonic image apparatus, as the number of synthetic beams is increased, resolution of a beam-forming image is improved in comparison to that of an image obtained by using conventional beam forming in the related art.

In the case of the conventional beam forming in the related art, one or more scan lines are generated by using data which is transmitted once. However, in the case of the synthetic aperture beam forming, after data are transmitted plural times corresponding to the number of synthetic beams, one scan line is generated by combining the data. Therefore, in the case where motion occurs at a target or an ultrasonic probe is moved during the transmission/reception periods, erroneous beam forming is performed. Accordingly, the quality of image is deteriorated according to a degree of motion in comparison to the image obtained by using the conventional beam forming in the related art.

Therefore, according to the embodiment of the present invention, in a system using synthetic aperture beam forming, motion in an image is detected, and the motion is displayed on a screen in various manners, so that a user can be allowed to actively adjust the number of synthetic beams. Namely, the user can be allowed to adjust the number of synthetic beams used for the synthetic aperture beam forming based on the measured degree of the motion.

Figure 1:
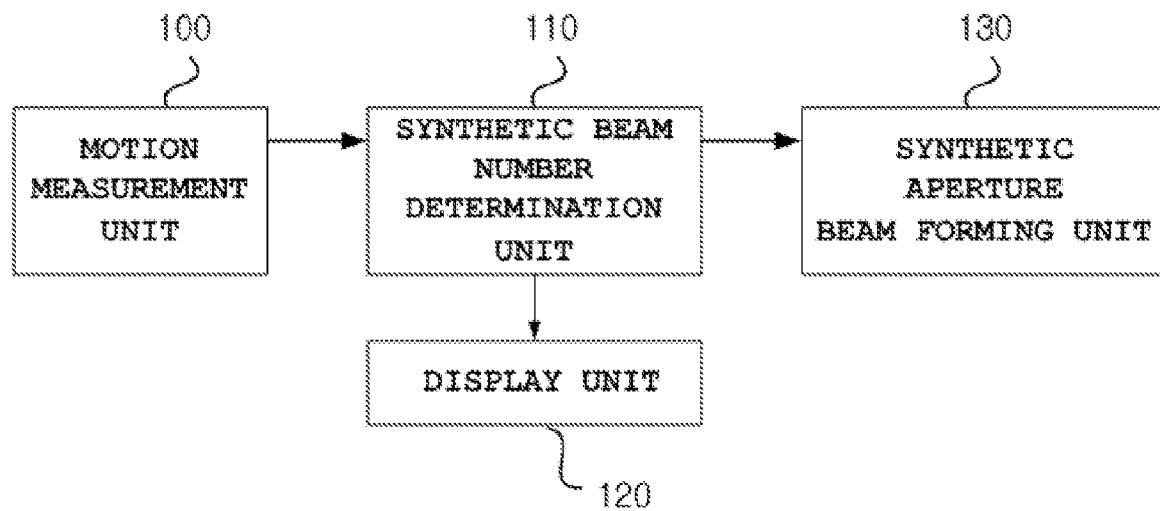
FIG. 1 is a diagram illustrating a configuration of a synthetic aperture beam forming apparatus which determines the number of synthetic beams according to a degree of motion according to an embodiment of the present invention.

FIG. 1 is a diagram illustrating a configuration of a synthetic aperture beam forming apparatus which determines the number of synthetic beams according to a degree of motion according to an embodiment of the present invention.

Referring to FIG. 1, the synthetic aperture beam forming apparatus is configured to include a motion measurement unit 100, a synthetic beam number determination unit 110, a display unit 120, and a synthetic aperture beam forming unit 130.

The motion measurement unit 100 measures a degree of motion in an output beam-forming image.

In order to observe an image of a fast-moving object by using synthetic aperture beam forming, the number of synthetic beams needs to be adjusted according to the degree of motion of the object.

In one method of measuring the degree of motion, a block matching algorithm can be used to compare an image of a previous frame to an image of a current frame. Each image is partitioned into blocks in units of certain pixels. Motion of blocks in each of the previous and current images is estimated in units of pixels by using various determination indexes such as sum of squares differences, minimum absolute difference, maximum matching pixel count, crosscorrelation, normalized correlation, and mutual correlation. The motion obtained in units of pixels can be converted into speed in cooperation with system parameters.

In another method of measuring the degree of motion, motion is measured by using correlation between focused signals by using various subapertures in scan lines or image points. In this method, first, a certain region of interest (ROI) is defined, and after that, representative motion of an object in the region of interest is measured. The representative motion is motion at a point where energy of a focused signal has the maximum value in the region of interest, and can be calculated by using crosscorrelation.

In still another method of measuring the degree of motion, representative axis-direction motion (or average motion speed) in a region of interest is estimated by using an autocorrelation based Doppler average frequency estimation method. Although the performance of the autocorrelation based motion estimation method is almost equal to that of the crosscorrelation method, the calculation amount thereof is greatly reduced, so that the autocorrelation based motion estimation method is useful for a real-time image.

In further still another method of measuring a degree of motion, when an original image having no blur is to be generated by calculating convolution between a point spread function (PSF) and a motion blur image, the point spread function is estimated, and the degree of motion is also estimated from the estimated point spread function.

When applying the synthetic aperture beam forming, the synthetic beam number determination unit 110 determines the number of synthetic beams from the measured degree of motion.

The relationship between the measured degree of motion of the object and the number of synthetic beams, which can be obtained a stabilized beam-forming image, is determined in advance to be stored in a table. On the other hand, the number of synthetic beams may be automatically determined with reference to the measured degree of motion in the table. In addition, if a user selects the optimum number of synthetic beams with reference to the display unit 120, the selected number of synthetic beams may become the number of synthetic beams determined by the synthetic beam number determination unit 110.

The display unit 120 displays the number of synthetic beams determined by the synthetic beam number determination unit 110.

The synthetic aperture beam forming unit 130 performs the beam forming by generating synthetic beams according to the number of synthetic beams determined by the synthetic beam number determination unit 110.

Figure 2:
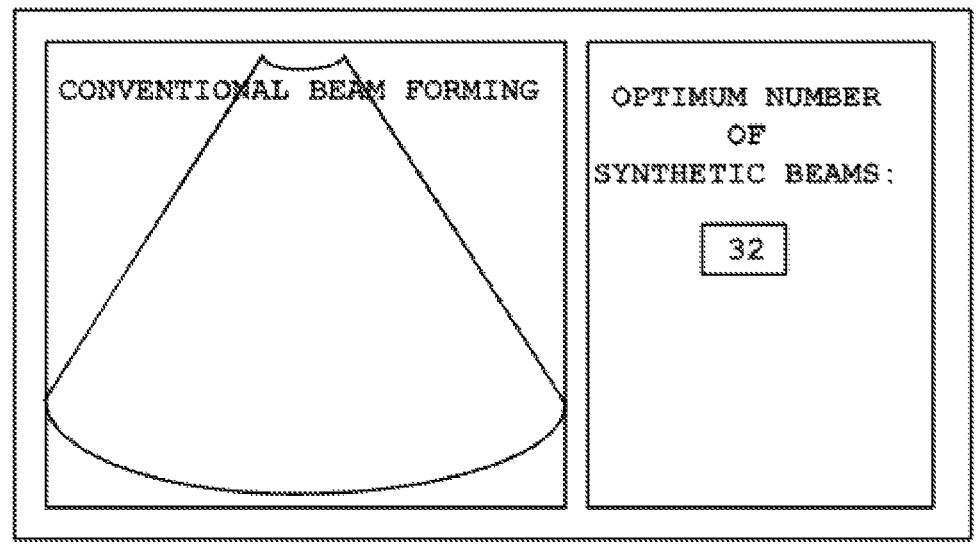
FIG. 2 is a diagram illustrating an example of a method of displaying stability of an image in the case of measuring a degree of motion in a conventional beam-forming image and applying synthetic aperture beam forming at a current position.
Figure 2:
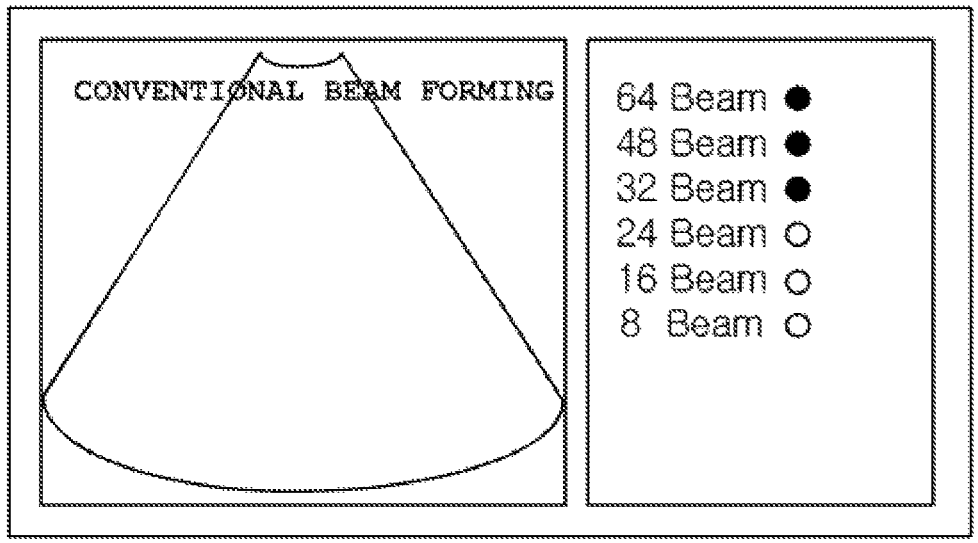

FIG. 2 is a diagram illustrating an example of a method of displaying stability of an image in the case of measuring a degree of motion in a conventional beam-forming image and applying the synthetic aperture beam forming at a current position.

As illustrated in (a) of FIG. 2, the number of synthetic beams which can be stably beam-formed at the current position can be informed. In addition, as illustrated in (b) of FIG. 2, stabilities at positions corresponding to the numbers of synthetic beams can be expressed by colors such as red, yellow, and green.

If the speed measured by the motion measurement unit is used, the number of synthetic beams which can be stably beam-formed can be derived from the degree of motion. The degree of motion and the optimum number of synthetic beams which can be stably beam-formed are stored in a table in a correspondence manner in advance.

Figure 3:
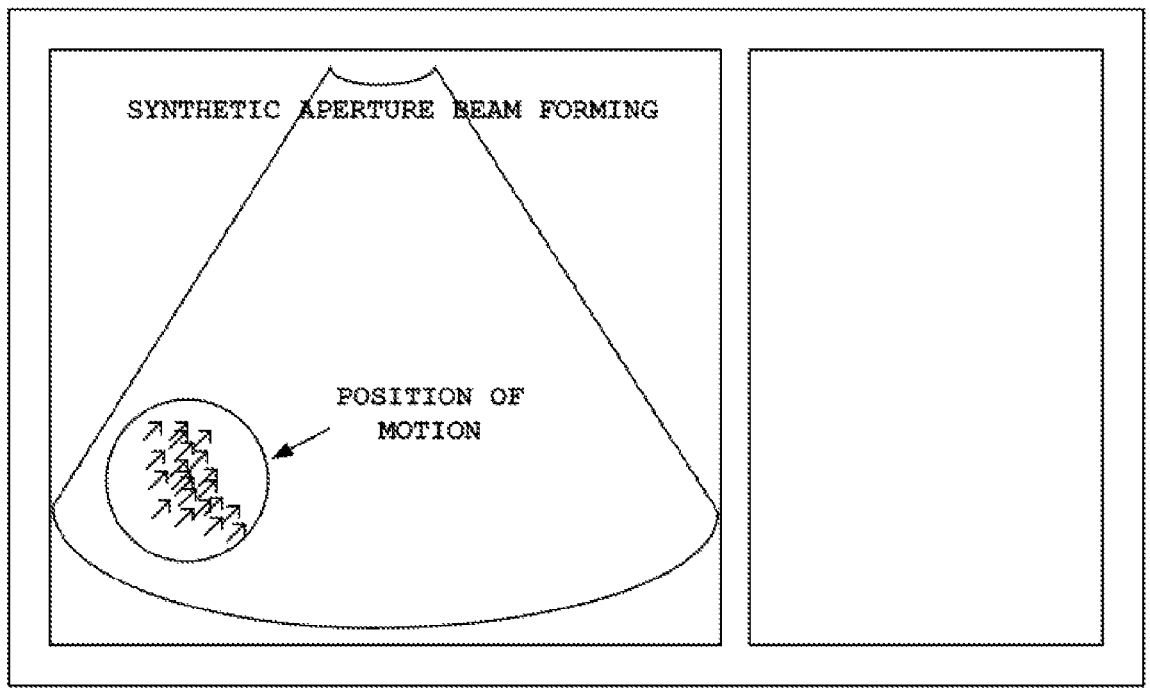
FIG. 3 is a diagram illustrating an example of a method of displaying motion in an image, to which synthetic aperture beam forming is applied, at positions of an actual image on a screen.

FIG. 3 is a diagram illustrating an example of a method of displaying motion in an image, to which the synthetic aperture beam forming is applied, at positions of an actual image.

As illustrated in FIG. 3, motion can be expressed in the image by arrows. If there are too much arrows, the user may adjust the number of synthetic beams by himself.

Figure 4:
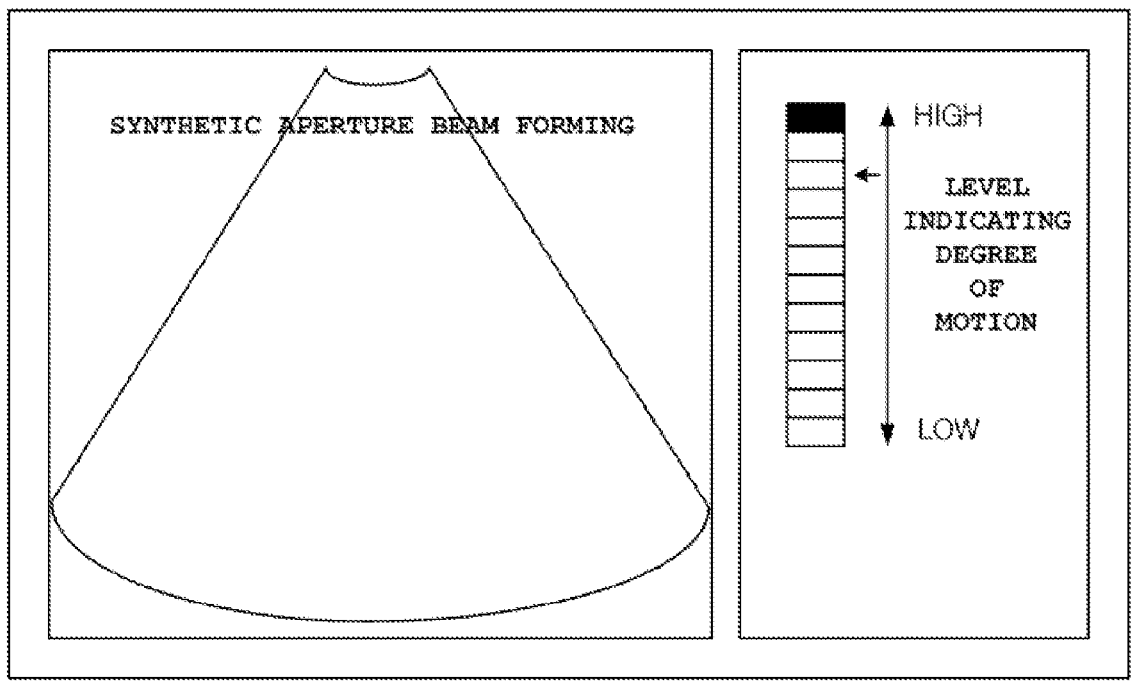
FIG. 4 is a diagram illustrating an example of a method of measuring a degree of motion in an image to which synthetic aperture beam forming is applied and displaying the degree of motion by using a parameter bar.

FIG. 4 is a diagram illustrating an example of measuring a degree of motion in an image to which synthetic aperture beam forming is applied and displaying the degree of motion by using a parameter bar.

Referring to FIG. 4, as illustrated in FIG. 2, the optimum number of synthetic beams is directly displayed in the image; or as illustrated in FIG. 3, a parameter bar indicating the degree of motion is displayed instead of directly displaying the degree of motion in the image.

FIG. 5 is a flowchart illustrating a synthetic aperture beam forming method of determining the number of synthetic beams according to a degree of motion according to another embodiment of the present invention.

As illustrated in FIG. 5, the synthetic aperture beam forming method according to the embodiment is configured to include steps which are performed in a time sequential manner by the synthetic aperture beam forming apparatus illustrated FIG. 1. Therefore, among the contents of the synthetic aperture beam forming apparatus described above with reference to FIG. 1, the omitted contents are also applied to the synthetic aperture beam forming method according to the embodiment of the present invention.

In Step 500, the synthetic aperture beam forming apparatus measures a degree of motion from an output beam-forming image.

After comparing an image of a previous frame to an image of a current frame in the beam-forming image by using a block matching algorithm, motion can be estimated in units of pixels. The obtained motion in units of pixels may be converted into a speed of a moving object in cooperation with system parameters.

In Step 510, the synthetic aperture beam forming apparatus determines the optimum number of synthetic beams when applying the synthetic aperture beam forming from the measured degree of motion. The relationship between the measured degree of motion of the object and the number of synthetic beams is determined in advance to be stored in a table.

In Step 520, the synthetic aperture beam forming apparatus displays the number of synthetic beams determined in Step 510.

Various methods of displaying the number of synthetic beams may be available as illustrated in FIGS. 2 to 4. As illustrated in FIG. 2, the optimum number of synthetic beams corresponding to motion may be directly displayed. In addition, as illustrated in FIG. 3, the degree of motion may be displayed at specific position by using arrows. In addition, as illustrated in FIG. 4, a parameter bar indicating the degree of motion can be displayed.

In Step 530, the synthetic aperture beam forming apparatus performs beam forming by generating synthetic beams according to the number of synthetic beams determined in Step 510.

The embodiments of the invention can also be embodied as computer readable program codes on a computer readable recording medium. The computer readable recoding medium may include program codes, data files, data structures, or a combination thereof. The program codes recorded on the recording medium may be program codes particularly designed and configured for the invention or program codes which are well known by the ordinarily skilled in the related art. Examples of the computer readable recording medium include magnetic media such as hard disk drives, floppy disks, and magnetic tapes, optical media such as CDROMs and DVDs, magneto-optical media such as floptical disks, read-only memories (ROMs), random-access memories (RAMs), flash memories, and hardware devices which are particularly configured to store the program codes. Examples of the program codes include high-level language codes which can be interpreted by interpreters and executed by computers as well as machine language codes produced by compilers. The hardware device may also be configured with one or more software modules for embodying the invention, and the reverse is available.

While the present invention has been particularly shown and described with reference to exemplary embodiments thereof, it will be understood by those skilled in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

The invention claimed is:

1. An apparatus of determining the number of synthetic beams for a synthetic aperture beam forming, comprising:
   a motion measurement unit which measures the degree of motion in an output beam-forming image;
   a synthetic beam number determination unit which determines the number of synthetic beams based on the measured degree of motion; and
   a display unit which displays the number of synthetic beams determined by the synthetic beam number determination unit.

2. The apparatus according to claim 1, wherein the synthetic beam number determination unit automatically determines the number of synthetic beams based on the measured degree of motion.

3. The apparatus according to claim 1, wherein the display unit displays stability of the beam-forming image corresponding to the number of synthetic beams, and
   wherein the number of synthetic beams selected by a user with reference to the stability corresponding to the number of synthetic beams is input to the synthetic beam number determination unit.

4. The apparatus according to claim 1,
   wherein the display unit displays the degree of motion by adjusting the number of arrows according to the degree of motion in the beam-forming image, and
   wherein the number of synthetic beams selected by a user with reference to the number of arrows is input to the synthetic beam number determination unit.

5. The apparatus according to claim 1,
   wherein the display unit displays the degree of motion by using a parameter bar, and
   wherein the number of synthetic beams selected by a user with reference to the parameter bar is input to the synthetic beam number determination unit.

6. The apparatus according to claim 1, wherein
   the motion measurement unit compares an image of a previous frame to an image of a current frame in the beam-forming image by using a block matching algorithm, and after that, measures the degree of motion by using a result of the comparison.

7. The apparatus according to claim 1, wherein
   the motion measurement unit measures the degree of motion by using correlation between focused beams by using a plurality of subapertures in scan lines or image points in the beam-forming image.

8. The apparatus according to claim 1, wherein the motion measurement unit measures representative motion in a region of interest, and the representative motion is motion at a point where energy of a focused signal has the maximum value in the region of interest.

9. The apparatus according to claim 1, wherein the motion measurement unit measures representative motion or an average motion speed in a region of interest by using an autocorrelation based Doppler average frequency estimation method.

10. The apparatus according to claim 1, wherein
a relationship between the measured degree of motion and the optimum number of synthetic beams is determined in advance to be stored in a table.

11. A synthetic aperture beam forming apparatus comprising:
a motion measurement unit which measures the degree of motion in an output beam-forming image;
a synthetic beam number determination unit which determines the number of synthetic beams based on the measured degree of motion in case of applying the synthetic aperture beam forming;
a display unit which displays the number of synthetic beams determined by the synthetic beam number determination unit; and
a synthetic aperture beam forming which performs beam forming by generating synthetic beams according to the number of synthetic beams determined by the synthetic beam number determination unit.

12. A method of determining the number of synthetic beams comprising steps of:
measuring the degree of motion of an output beam-forming image;
determining the number of synthetic beams based on the measured degree of motion in case of applying the synthetic aperture beam forming; and
displaying the determined number of synthetic beams.

13. The method according to claim 12, wherein the step of displaying includes steps of:
displaying stability of the beam-forming image corresponding to the number of synthetic beams; and
inputting the number of synthetic beams selected by a user with reference to the stability corresponding to the number of synthetic beams to an apparatus of determining the number of synthetic beams.

14. The method according to claim 12, wherein
the step of displaying includes steps of:
displaying the degree of motion by representing the number of arrows according to the degree of motion in the beam-forming image; and
inputting the number of synthetic beams selected by a user with reference to the number of arrows to an apparatus of determining the number of synthetic beams.

15. The method according to claim 12, wherein
the step of displaying includes steps of:
displaying the degree of motion by using a parameter bar; and
inputting the number of synthetic beams selected by a user with reference to the parameter bar to an apparatus of determining the number of synthetic beams.

16. A synthetic aperture beam forming method, comprising steps of:
measuring the degree of motion of an output beam-forming image;
determining the optimum number of synthetic beams based on the measured degree of motion in case of applying the synthetic aperture beam forming;
displaying the determined number of synthetic beams; and
performing beam forming by generating the synthetic beam according to the determined number of synthetic beams.

17. A non-transitory computer-readable recording medium with a program recorded thereon for allowing a computer to execute the method according to claim 12.

\* \* \* \* \*